United States Patent [19]

Bilweis

[11] Patent Number: 5,196,003
[45] Date of Patent: Mar. 23, 1993

[54] ENDOSCOPIC SURGICAL INSTRUMENT FOR TAKING HOLD OF TISSUE

[75] Inventor: Joseph Bilweis, Noisy Le Roi, France

[73] Assignee: Ethicon, Inc., Somerville, N.J.

[21] Appl. No.: 787,450

[22] Filed: Nov. 4, 1991

[30] Foreign Application Priority Data

Nov. 6, 1990 [FR] France .................. 90 13712

[51] Int. Cl.⁵ .................................. A61B 17/00
[52] U.S. Cl. ........................ 606/1; 606/123; 128/204.28; 604/313; 604/316; 604/902
[58] Field of Search ............ 606/1, 107, 121–123, 606/205; 604/37, 74, 75, 313, 316, 902, 73, 118, 217; 128/204.18, 205.13, 205.14, 203.28, 204.28, 205.17

[56] References Cited

U.S. PATENT DOCUMENTS

| | | | |
|---|---|---|---|
| 2,379,629 | 7/1945 | Eweson | 606/107 |
| 2,555,076 | 5/1951 | Crossley | 606/107 |
| 3,090,380 | 5/1963 | Dold | 128/205.13 |
| 3,129,971 | 4/1964 | Kobler | 606/107 |
| 3,139,298 | 6/1964 | Grabiel | 606/107 |
| 4,047,532 | 9/1977 | Phillips et al. | 606/107 |

FOREIGN PATENT DOCUMENTS

| | | |
|---|---|---|
| 3920919 | 1/1990 | Fed. Rep. of Germany ...... 606/107 |
| 3920919A | 11/1990 | Fed. Rep. of Germany . |
| 1388858 | 3/1975 | United Kingdom . |

*Primary Examiner*—Stephen C. Pellegrino
*Assistant Examiner*—Glenn Dawson
*Attorney, Agent, or Firm*—Emil Richard Skula

[57] ABSTRACT

A surgical instrument, in particular for endoscopic surgery, wherein the instrument comprises a tube provided at its proximal end with a flexible suction cup and at its distal end with a bulb such that the volume of the bulb is in communication with the suction cup via the tube in order to enable the suction cup to be applied against and to adhere to tissues or organs for displacment under the control of pressure and/or suction from the bulb.

10 Claims, 1 Drawing Sheet

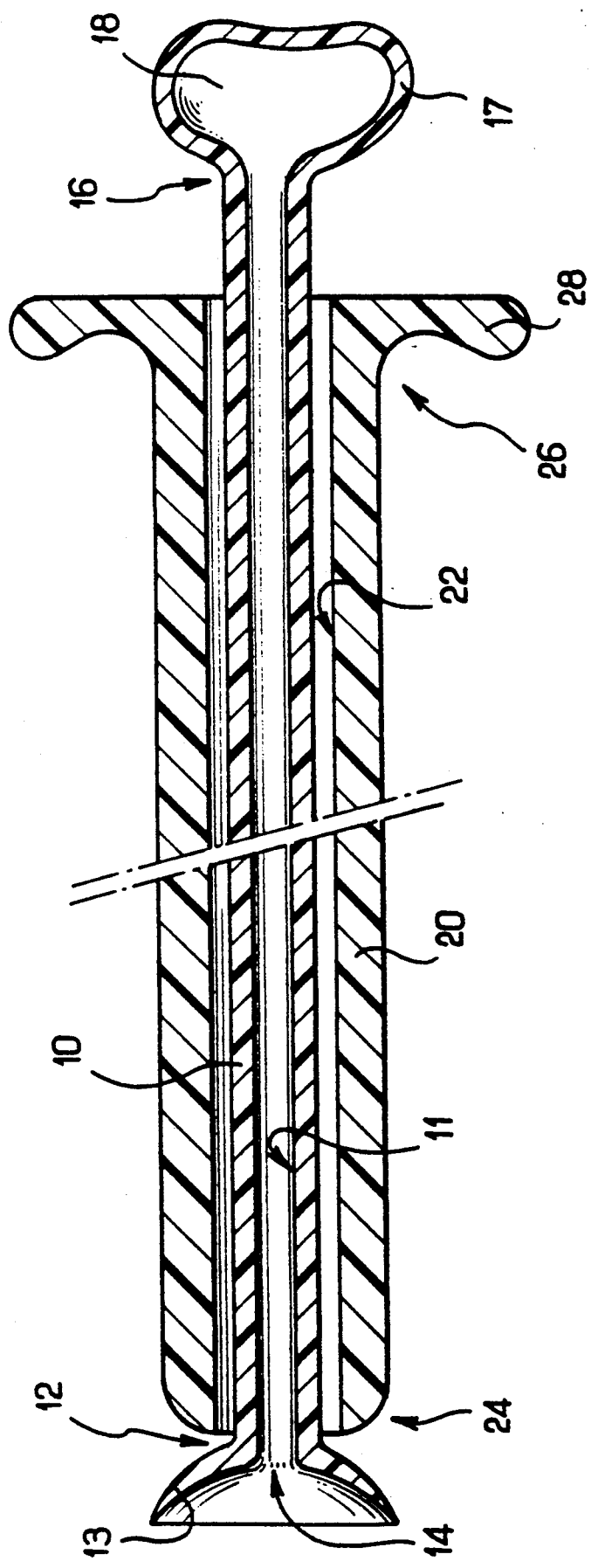
FIG._1

ENDOSCOPIC SURGICAL INSTRUMENT FOR TAKING HOLD OF TISSUE

The present invention relates to the field of surgical instruments.

The present invention relates more particularly to the field of endoscopic surgery.

BACKGROUND OF THE INVENTION

Surgeons are aware that the instruments proposed so far for taking hold of and/or displacing tissues and/or organs, particularly during endoscopic surgery, do not give full satisfaction.

These instruments are generally in the form of forceps or the equivalent and they frequently traumatize the tissues or the organs they have taken hold of.

An object of the present invention is to eliminate the drawbacks of known prior instruments.

SUMMARY OF THE INVENTION

According to the present invention, this object is achieved by a surgical instrument, in particular for endoscopic surgery, comprising a tube provided at its proximal end with a flexible suction cup and at its distal end with a bulb such that the volume of the bulb is in communication with the suction cup via the tube in order to enable the suction cup to be applied against and to adhere to tissues or organs for displacement under the control of pressure and/or suction from the bulb.

As used herein, the convention concerning the terms "proximal" and "distal" relates to being near or far from the site at which surgery is being performed. The active part of the instrument is said to be at its "proximal" end, the part held by the surgeon is said to be at its "distal" end.

BRIEF DESCRIPTION OF THE DRAWING

An embodiment of the invention is described by way of example with reference to the sole figure of the accompanying drawing which shows an instrument of the present invention in axial longitudinal section by way of non-limiting example.

DETAILED DESCRIPTION

The accompanying figure shows an instrument suitable for taking hold of or displacing tissues or organs of a living being and essentially comprising a tube 10 provided at its proximal end 12 with a suction cup 13 and provided at its distal end 16 with a bulb 17.

The suction cup 13 is in the form of a concave cap provided with a central orifice 14 such that the suction cup 13 communicates with the inside volume 18 of the bulb 17 via the longitudinal channel 11 inside the tube 10.

The representation given in the figure is naturally merely diagrammatic. IN particular, the relative dimensions of the diameter of the tube 10, of the suction cup 13, and of the bulb 17 as shown diagrammatically in the figure are not limiting in any way.

The tube 10, the suction cup 13, and the bulb 17 are preferably made as a single piece. Nevertheless, the tube 10, the suction cup 13, and the bulb 17 could be made in the form of pieces that are initially separate and are then assembled together by any technique known to the person skilled in the art.

The material from which the suction cup 13 and the bulb 17 are made must be an elastic flexible material to enable these components to return to a rest position after they have been acted on. The material from which the suction cup 13 and the bulb 17 are made is preferably rubber.

Advantageously, as shown diagrammatically in the figure, the tube 10 is placed in the lumen 22 of a cannula 20. There are numerous different ways in which the cannula 20 can be made.

The proximal end 24 of the cannula 20 is rounded to avoid the suction cup 13 injuring the tissues or organs it takes hold of and also the tissues or organs surrounding those that it takes hold of. The cannula 20 is also preferably provided at its distal end 26 with handle means, e.g. a collar 28.

As shown in the figure, the tube 10 emerges from both ends of the cannula 20 so that the suction cup 13 is accessible at the proximal end of the cannula 20 while the bulb 17 is accessible at the distal end thereof.

Where appropriate, the tube 10 may be placed in a cannula 20 having a plurality of separate longitudinal lumens, with the other lumens being suitable for use in conventional manner e.g. to convey a flow of fluid for treatment or for sampling purposes.

To take hold of tissue or any organ by means of the suction cup 13, it suffices merely to compress the bulb 17 at least in part and then to apply the suction cup against the tissue or the organ to be taken hold of while simultaneously releasing the bulb 17. Thereafter, to release the tissue or the organ that has been taken hold of in this way, it suffices merely to compress the bulb 17 again.

By taking hold of tissue or an organ by suction by means of the suction cup 13, it is possible in complete safety to avoid any trauma of tissues or organs that are taken hold of.

Naturally, the present invention is limited to the particular embodiments described above, but extends to any variant coming within the spirit of the invention.

I claim:

1. A surgical instrument wherein the instrument comprises a tube having a proximal end and a distal end, said tube placed in a cannula and having its proximal end and its distal end emerging from the cannula, said tube provided at its proximal end with a flexible suction cup in the form of a concave cap provided with a central orifice and said tube provided at its distal end with a bulb having an inside volume in communication with said central orifice via said tube in order to enable said suction cup to be applied against and to adhere to tissues or organs for displacement under the control of pressure and/or suction from the bulb.

2. A surgical instrument according to claim 1, wherein the tube, the suction cup, and the bulb comprise a single piece.

3. An instrument according to claim 2, wherein the suction cup comprises rubber.

4. An instrument according to claim 2, wherein the bulb comprises rubber.

5. An instrument according to claim 1, wherein the tube, the suction cup, and the bulb are separate pieces.

6. An instrument according to claim 5, wherein the suction cup comprises rubber.

7. An instrument according to claim 5, wherein the bulb comprises rubber.

8. An instrument according to claim 1, wherein the suction cup comprises rubber.

9. An instrument according to claim 8, wherein the bulb comprises rubber.

10. An instrument according to claim 1, wherein the bulb comprises rubber.

* * * * *